(12) United States Patent
Shevkoplyas et al.

(10) Patent No.: US 8,828,226 B2
(45) Date of Patent: *Sep. 9, 2014

(54) SYSTEM FOR ASSESSING THE EFFICACY OF STORED RED BLOOD CELLS USING MICROVASCULAR NETWORKS

(75) Inventors: Sergey Shevkoplyas, New Orleans, LA (US); Tatsuro Yoshida, West Newton, MA (US); Mark Bitensky, Waltham, MA (US)

(73) Assignee: The Trustees of Boston University, Boston, MA (US)

(*) Notice: Subject to any disclaimer, the term of this patent is extended or adjusted under 35 U.S.C. 154(b) by 147 days.

This patent is subject to a terminal disclaimer.

(21) Appl. No.: 12/386,108

(22) Filed: Apr. 14, 2009

(65) Prior Publication Data

US 2009/0269837 A1    Oct. 29, 2009

Related U.S. Application Data

(63) Continuation-in-part of application No. 10/377,178, filed on Mar. 1, 2003, now Pat. No. 7,517,453.

(51) Int. Cl.
| | | |
|---|---|---|
| *B01D 63/00* | (2006.01) | |
| *G01N 33/48* | (2006.01) | |
| *B01D 63/08* | (2006.01) | |
| *B01L 3/00* | (2006.01) | |
| *G01N 33/80* | (2006.01) | |
| *G01N 11/08* | (2006.01) | |

(52) U.S. Cl.
CPC ............ *B01D 63/088* (2013.01); *B01L 3/5027* (2013.01); *G01N 33/80* (2013.01); *B01L 2200/0647* (2013.01); *B01L 2300/0861* (2013.01); *B01L 2400/0439* (2013.01); *B01L 2300/123* (2013.01); *G01N 11/08* (2013.01); *Y10S 707/99945* (2013.01); *Y10S 707/99948* (2013.01)
USPC ....... 210/321.6; 435/287.1; 435/29; 382/134; 702/21; 707/999.104; 707/999.107

(58) Field of Classification Search
None
See application file for complete search history.

(56) References Cited

U.S. PATENT DOCUMENTS

| | | | |
|---|---|---|---|
| 4,086,924 | A | 5/1978 | Latham, Jr. |
| 4,228,032 | A | 10/1980 | Talcott |

(Continued)

FOREIGN PATENT DOCUMENTS

| | | |
|---|---|---|
| DE | 3722984 | 1/1989 |
| EP | 0 100 419 A2 | 2/1984 |

(Continued)

OTHER PUBLICATIONS

Countless Cell Counting Chamber Slides for Countless Automated Cell Counter—box of 20, Invitrogen Corporation, The Handbook (1): 15.3 Viability and Cytotoxicity Assay Kits for Diverse Cell Types, 2008 (1 pp).

(Continued)

*Primary Examiner* — Krishnan S Menon
(74) *Attorney, Agent, or Firm* — Arnold & Porter LLP

(57) ABSTRACT

A system for assessing the microvascular fitness of a sample of stored red blood cells. The system has a network device having at least one network unit. The network unit has a single inlet and a single outlet for the sample and a plurality of microchannels. The plurality of microchannels receive the sample from the single inlet and drain the sample into the single outlet. The network unit includes an aspiration pressure means for providing movement of liquid sample through the at least one network unit. The system further includes an analysis unit that receives the network device therein. The analysis unit includes a sensor for capturing measurements related to the sample and a processor capable of comparing the captured measurements to measurements stored in a database of healthy red blood cells to determine the microvascular fitness of the stored red blood cells.

38 Claims, 6 Drawing Sheets

(56) References Cited

U.S. PATENT DOCUMENTS

| | | |
|---|---|---|
| 4,300,559 A | 11/1981 | Gajewski et al. |
| 4,370,160 A | 1/1983 | Ziemelis |
| 4,381,775 A | 5/1983 | Nose' et al. |
| 4,540,416 A | 9/1985 | Hattori et al. |
| 4,572,899 A | 2/1986 | Walker et al. |
| 4,585,735 A | 4/1986 | Meryman et al. |
| 4,654,053 A | 3/1987 | Sievers et al. |
| 4,670,013 A | 6/1987 | Barnes et al. |
| 4,701,267 A | 10/1987 | Watanabe et al. |
| 4,713,176 A | 12/1987 | Schoendorfer et al. |
| 4,748,121 A | 5/1988 | Beaver et al. |
| 4,749,551 A | 6/1988 | Borgione |
| 4,769,175 A | 9/1988 | Inoue |
| 4,769,318 A | 9/1988 | Hamasaki et al. |
| 4,837,047 A | 6/1989 | Sato et al. |
| 4,880,548 A | 11/1989 | Pall et al. |
| 4,880,786 A | 11/1989 | Sasakawa et al. |
| 4,902,701 A | 2/1990 | Batchelor et al. |
| 4,925,572 A | 5/1990 | Pall |
| 5,000,848 A | 3/1991 | Hodgins et al. |
| 5,023,054 A | 6/1991 | Sato et al. |
| 5,037,419 A | 8/1991 | Valentine et al. |
| 5,152,905 A | 10/1992 | Pall et al. |
| 5,192,320 A | 3/1993 | Anazawa et al. |
| 5,208,335 A | 5/1993 | Ramprasad et al. |
| 5,229,012 A | 7/1993 | Pall et al. |
| 5,254,248 A | 10/1993 | Nakamura et al. |
| 5,353,793 A | 10/1994 | Bornn |
| 5,356,375 A | 10/1994 | Higley |
| 5,360,734 A | 11/1994 | Chapman et al. |
| 5,362,442 A | 11/1994 | Kent |
| 5,386,014 A | 1/1995 | Nho et al. |
| 5,387,624 A | 2/1995 | Morita et al. |
| 5,417,986 A | 5/1995 | Reid et al. |
| 5,427,663 A | 6/1995 | Austin et al. |
| 5,443,743 A | 8/1995 | Gsell |
| 5,476,764 A | 12/1995 | Bitensky |
| 5,506,141 A | 4/1996 | Weinreb et al. |
| 5,529,821 A | 6/1996 | Ishikawa et al. |
| 5,617,873 A | 4/1997 | Yost et al. |
| 5,624,794 A | 4/1997 | Bitensky et al. |
| 5,635,358 A * | 6/1997 | Wilding et al. ............ 435/7.2 |
| 5,691,452 A | 11/1997 | Gawryl et al. |
| 5,693,230 A | 12/1997 | Asher |
| 5,698,250 A | 12/1997 | DelDuca et al. |
| 5,730,989 A | 3/1998 | Wright |
| 5,750,115 A | 5/1998 | Van Den Bosch |
| 5,783,094 A | 7/1998 | Kraus et al. |
| 5,783,148 A | 7/1998 | Cottingham et al. |
| 5,789,151 A | 8/1998 | Bitensky et al. |
| 5,811,142 A | 9/1998 | DelDuca et al. |
| 5,846,427 A | 12/1998 | Kessler et al. |
| 5,972,710 A | 10/1999 | Weigl et al. |
| 6,027,623 A | 2/2000 | Ohkawa |
| 6,047,203 A | 4/2000 | Sackner et al. |
| 6,090,062 A | 7/2000 | Sood et al. |
| 6,150,085 A | 11/2000 | Hess et al. |
| 6,162,396 A | 12/2000 | Bitensky et al. |
| 6,187,572 B1 | 2/2001 | Platz et al. |
| 6,210,601 B1 | 4/2001 | Hottle et al. |
| 6,231,770 B1 | 5/2001 | Bormann et al. |
| 6,254,628 B1 | 7/2001 | Wallace et al. |
| 6,337,026 B1 | 1/2002 | Lee et al. |
| 6,358,678 B1 | 3/2002 | Bakaltcheva et al. |
| 6,368,871 B1 | 4/2002 | Christel et al. |
| 6,387,461 B1 | 5/2002 | Ebner et al. |
| 6,403,124 B1 | 6/2002 | Dottori |
| 6,413,713 B1 | 7/2002 | Serebrennikov |
| 6,439,577 B2 | 8/2002 | Jorgensen et al. |
| 6,447,987 B1 | 9/2002 | Hess et al. |
| 6,468,732 B1 | 10/2002 | Malin et al. |
| 6,475,147 B1 | 11/2002 | Yost et al. |
| 6,482,585 B2 | 11/2002 | Dottori |
| 6,527,957 B1 | 3/2003 | Denienga et al. |
| 6,564,207 B1 | 5/2003 | Abdoh |
| 6,610,772 B1 | 8/2003 | Clauberg et al. |
| 6,688,476 B2 | 2/2004 | Breillatt, Jr. et al. |
| 6,695,803 B1 | 2/2004 | Robinson et al. |
| 6,697,667 B1 | 2/2004 | Lee et al. |
| 6,723,051 B2 | 4/2004 | Davidson et al. |
| 6,761,695 B2 | 7/2004 | Yost et al. |
| 6,773,407 B2 | 8/2004 | Yost et al. |
| 6,817,979 B2 | 11/2004 | Nihtilä |
| 6,866,783 B2 | 3/2005 | Baurmeister et al. |
| 6,955,648 B2 | 10/2005 | Mozayeni et al. |
| 7,104,958 B2 | 9/2006 | Crutchfield et al. |
| 7,208,120 B2 | 4/2007 | Bitensky et al. |
| 7,347,887 B2 | 3/2008 | Bulow et al. |
| 7,361,277 B2 | 4/2008 | Bormann et al. |
| 7,431,995 B2 | 10/2008 | Smith et al. |
| 7,452,601 B2 | 11/2008 | Ebner et al. |
| 7,721,898 B2 | 5/2010 | Yagi et al. |
| 7,723,017 B2 | 5/2010 | Bitensky et al. |
| 7,754,798 B2 | 7/2010 | Ebner et al. |
| 7,775,376 B2 | 8/2010 | Bonaguidi et al. |
| 8,071,282 B2 | 12/2011 | Bitensky et al. |
| 2001/0027156 A1 | 10/2001 | Egozy et al. |
| 2001/0049089 A1 | 12/2001 | Dottori |
| 2002/0062078 A1 | 5/2002 | Crutchfield et al. |
| 2002/0066699 A1 | 6/2002 | Boggs et al. |
| 2002/0085952 A1 | 7/2002 | Ellingboe et al. |
| 2002/0086329 A1 | 7/2002 | Shvets et al. |
| 2002/0099570 A1 | 7/2002 | Knight |
| 2002/0182241 A1 | 12/2002 | Borenstein et al. |
| 2003/0003575 A1 | 1/2003 | Vacanti et al. |
| 2003/0062299 A1 | 4/2003 | Lee et al. |
| 2003/0106861 A1 | 6/2003 | Gibbs et al. |
| 2003/0124504 A1 | 7/2003 | Bitensky et al. |
| 2003/0183801 A1 | 10/2003 | Yang et al. |
| 2003/0189003 A1 | 10/2003 | Kraus et al. |
| 2004/0026341 A1 | 2/2004 | Hogberg et al. |
| 2004/0168982 A1* | 9/2004 | Bitensky et al. ............ 210/649 |
| 2005/0038342 A1 | 2/2005 | Mozayeni et al. |
| 2005/0137517 A1 | 6/2005 | Blickhan et al. |
| 2005/0139806 A1 | 6/2005 | Havens et al. |
| 2005/0208462 A1 | 9/2005 | Bitensky et al. |
| 2005/0230856 A1 | 10/2005 | Parekh et al. |
| 2005/0233302 A1 | 10/2005 | Hess et al. |
| 2006/0081524 A1 | 4/2006 | Sengupta et al. |
| 2006/0118479 A1 | 6/2006 | Shevkoplyas et al. |
| 2007/0078113 A1 | 4/2007 | Roth et al. |
| 2008/0108930 A1* | 5/2008 | Weitzel et al. ............ 604/5.04 |
| 2008/0160107 A1 | 7/2008 | McCaney et al. |
| 2008/0243045 A1 | 10/2008 | Pasqualini |
| 2009/0017128 A1 | 1/2009 | Monzyk et al. |
| 2010/0221697 A1 | 9/2010 | Sehgal |
| 2010/0313755 A1 | 12/2010 | Koros et al. |
| 2012/0024156 A1 | 2/2012 | Yoshida et al. |
| 2012/0129148 A1 | 5/2012 | Hess et al. |
| 2012/0219633 A1 | 8/2012 | Sowemimo-Coker |

FOREIGN PATENT DOCUMENTS

| | | | |
|---|---|---|---|
| EP | 0 217 759 | A1 | 4/1987 |
| EP | 0 299 381 | A2 | 1/1989 |
| EP | 0 890 368 | A1 | 1/1999 |
| EP | 1 109 447 | B1 | 10/2003 |
| FR | 2 581 289 | A1 | 11/1986 |
| GB | 1 044 649 | A2 | 10/1966 |
| JP | 58-194879 | | 11/1983 |
| JP | 63-63616 | A | 3/1988 |
| JP | 01-104271 | A | 4/1989 |
| JP | 5-503075 | A | 5/1993 |
| JP | 5-503304 | A | 6/1993 |
| JP | 5-305123 | A | 11/1993 |
| JP | 06-121920 | A | 5/1994 |
| JP | 2700170 | B2 | 1/1998 |
| JP | 2000-516963 | A | 12/2000 |
| JP | 2002-253936 | A | 9/2002 |
| JP | 2005-535279 | A | 11/2005 |
| KR | 10-0721054 | | 5/2006 |
| SU | 1718766 | A1 | 1/1990 |
| WO | WO 81/02239 | A1 | 8/1981 |
| WO | WO 86/00809 | A1 | 2/1986 |

(56) References Cited

FOREIGN PATENT DOCUMENTS

| WO | WO 89/02274 A1 | 3/1989 |
|---|---|---|
| WO | WO 91/04659 A1 | 4/1991 |
| WO | WO 92/08348 A1 | 5/1992 |
| WO | WO 95/29662 A2 | 11/1995 |
| WO | WO 96/29864 A1 | 10/1996 |
| WO | WO 99/48963 A2 | 9/1999 |
| WO | WO 03/043571 A2 | 5/2003 |
| WO | WO 2006-057473 A1 | 6/2006 |
| WO | WO 2011/014855 A2 | 2/2011 |

OTHER PUBLICATIONS

Shevkoplyas et al., Direct Measurement of the Impact of Impaired Erythrocyte Deformability on Microvascular Network Perfusion in a Microfluidic Device, The Royal Society of Chemistry 2006: Lab Chip, 2006, 6, (pp. 914-920).

Wang, et al., *Fabrication of PLGA Microvessel Scaffolds with Circular Microchannels using Soft Lithography*. Journal of Micromechanics and Microengineering, 2007, vol. 17 (pp. 2000-2005).

Jain, et al., *Determinants of Leukocyte Margination in Rectangular Microchannels*. PLoS ONE, Sep. 2009, vol. 4, No. 9 (pp. 1-8).

International Search Report and Written Opinion dated Aug. 4, 2010 from corresponding PCT Application No. PCT/US2010/31055.

International Preliminary Report on Patentability dated Oct. 27, 2011 from corresponding International Application No. PCT/US2010/031055.

Alcantar et al., "Polyethylene glycol-coated biocompatible surfaces," *Journal of Biomedical Materials Research*, 51(3):343-351 (2000).

Anderson et al., "Microfabrication and microfluidics for tissue engineering: state of the art and future opportunities," *Lab Chip*, 4:98-103 (2004).

Barbee et al., "The Fahraeus Effect," *Microvascular Research*, 3:6-16 (1971).

Barclay et al., "A Method for Detecting Chaos in Canine Myocardial Microcirculatory Red Cell Flux," *Microcirculation*, 7(5):335-346 (2000).

Bardy et al., "Technetium-99m Labeling by Means of Stannous Pyrophosphate: Application to Bleomycin and Red Blood Cells," *Journal of Nuclear Medicine*, 16(5):435-437 (1975).

Barras et al., "Einfluss der Rejuvenation auf die rheologischen Eigenschaften gelagerter Erythrozyten," *VASA*, 23(4):305-311 (1994).

Beutler et al., "Storage of red cell concentrates in CPD-A2 for 42 and 49 days," *The Journal of Laboratory and Clinical Medicine*, 102(1):53-62 (1983).

Borenstein et al., "Microfabrication Technology for Vascularized Tissue Engineering," *Biomedical Microdevices*, 4(3):167-175 (2002).

Brody et al., "Deformation and Flow of Red Blood Cells in a Synthetic Lattice: Evidence for an Active Cytoskeleton," *Biophysical Journal*, 68:2224-2232 (1995).

Carmen, "The Selection of Plastic Materials for Blood Bags," *Transfusion Medicine Reviews*, 7(1):1-10 (1993).

Carr et al., "Nonlinear Dynamics of Microvascular Blood Flow," *Annals of Biomedical Engineering*, 28:641-652 (2000).

Chilton et al., "Privacy Protection of Health Information: Patient Rights and Pediatrician Responsibilities," *Pediatrics*, 104(4):973-977 (1999).

Cokelet et al., "Fabrication of in Vitro Microvascular Blood Flow Systems by Photolithography," *Microvascular Research*, 46:394-400 (1993).

Dale et al., "Human Vaccination with *Escherichia coli* J5 Mutant Induces Cross-Reactive Bactericidal Antibody against *Neisseria gonorrhoeae* Lipooligosaccharide," *The Journal of Infectious Diseases*, 166:316-325 (1992).

De Angelis et al., "Erythrocyte Shape Control in Stored Blood: The Effect of Additive Solutions on Shape Recovery," *Haematologica*, 73:7-12 (1988).

Deible et al., "Molecular barriers to biomaterial thrombosis by modification of surface proteins with polyethylene glycol," *Biomaterials*, 19:1885-1893 (1998).

De Venuto et al., "Rejuvenation of Human Red Blood Cells During Liquid Storage," *Transfusion*, 14(4):338-344 (1974).

Dumaswala et al., "Studies in Red Blood Cell Preservation: 9. The Role of Glutamine in Red Cell Preservation," *Vox Sang*, 67:255-259 (1994).

Dumaswala et al., "Glutamine- and Phosphate-Containing Hypotonic Storage Media Better Maintain Erythrocyte Membrane Physical Properties," *Blood*, 88(2):697-704 (1996).

Dumaswala et al., "Improved Red Blood Cell Preservation Correlates With Decreased Loss of Bands 3, 4.1, Acetylcholinestrase, and Lipids in Microvesicles," *Blood*, 87(4):1612-1616 (1996).

Dumont et al., "Anaerobic storage of red blood cells in a novel additive solution improves in vivo recovery," *Transfusion*, 49(3):458-464 (2009).

Effenhauser et al., "Integrated Capillary Electrophoresis on Flexible Silicone Microdevices: Analysis of DNA Restriction Fragments and Detection of Single DNA Molecules on Microchips," *Anal. Chem.*, 69:3451-3457 (1997).

European Search Report completed on Feb. 11, 2005, in European Patent Application No. 02 78 2307.9.

Fahraeus et al., "The Viscosity of the Blood in Narrow Capillary Tubes," *Am. J. Physiol.*, 96(3):562-568 (1931).

Fang et al., "Inhibition of Lipopolysaccharide-Associated Endotoxin Activities In Vitro and In Vivo by the Human Anti-Lipid A Monoclonal Antibody SdJ5-1.17.15," *Infection and Immunity*, 61(9):3873-3878 (1993).

Frame et al., "A System for Culture of Endothelial Cells in 20-50-µm Branching Tubes," *Microcirculation*, 2(4):377-385 (1995).

Fung et al., "High-Resolution Data on the Geometry of Red Blood Cells", *Biorheology*, 18:369-385 (1981).

Gañán-Calvo et al., "Current and Droplet Size in the Electrospraying of Liquids. Scaling Laws," *J. Aerosol Sci.*, 28(2):249-275 (1997).

Green et al., "10. Liposomal Vaccines," Immunobiology of Proteins and Peptides VII, Plenum Press, New York, pp. 83-92 (1995).

Greenwalt et al., "Studies in Red Blood Cell Preservation. 7. In vivo and in Vitro Studies with a Modified Phosphate-Ammonium Additive Solution," *Vox Sang*, 65:87-94 (1993).

Greenwalt et al., "Studies in Red Blood Cell Preservation. 8. Liquid Storage of Red Cells in Glycerol-Containing Additive Solution," *Vox. Sang*, 67:139-143 (1994).

Greenwalt et al., "Studies in red blood cell preservation. 10. $^{51}$Cr Recovery of Red Cells after Liquid Storage in a Glycerol-Containing Additive Solution," *Vox Sang*, 70:6-10 (1996).

Greenwalt et al., "The effect of hypotonicity, glutamine, and glycine on red cell preservation," Transfusion, 37:269-276 (1997).

Griffith, "Temporal chaos in the microcirculation," *Cardiovascular Research*, 31:342-358 (1996).

Hamasaki et al., "Acid-citrate-dextrose-phosphoenolpyruvate medium as a rejuvenant for blood storage," *Transfusion*, 23(1):1-7 (1983).

Hess, "Extended Liquid Storage of Red Blood Cells," Blood Donors and the Supply of Blood and Blood Products, National Academy Press, Washington, D.C., pp. 99-102 (1996).

Hess et al., "Successful storage of RBCs for 9 weeks in a new additive solution," *Transfusion*, 40:1007-1011 (2000).

Hess, "Storage of red blood cells under anaerobic conditions," *Vox Sanguinis*, 93:183 (2007).

Hodgson et al., "Prophylactic use of human endotoxin-core hyperimmune gammaglobulin to prevent endotoxaemia in colostrum-deprived, gnotobiotic lambs challenged orally with *Escherichia coli*," *FEMS Immunology and Medical Microbiology*, 11:171-180 (1995).

Högman et al., "Cell Shape and Total Adenylate Concentration as Important Factors for Posttransfusion Survival of Erythrocytes," *Biomed. Biochim. Acta*, 42:S327-S331 (1983).

Högman et al.,"Effects of Oxygen on Red Cells during Liquid Storage at +4° C.," *Vox Sang.*, 51:27-34 (1986).

Högman et al., "Effects of Oxygen and Mixing on red cells stored in plastic bags at +4° C.," *Biomed. Biochim. Acta.*, 46:S290-S294 (1987).

Högman et al., "Shall Red Cell Units Stand Upright, Lie Flat or be Mixed During Storage? In Vitro Studies of Red Cells Collected in 0.5 CPD and Stored in RAS2 (Erythrosol®)," *Transfus. Sci.*, 16(2):193-199 (1995).

Huang et al., "Continuous Particle Separation Through Deterministic Lateral Displacement," *Science*, 304:987-990 (2004).

International Preliminary Report on Patentability completed on Feb. 14, 2012, in International Patent Application No. PCT/US2010/52084.

(56) References Cited

OTHER PUBLICATIONS

International Preliminary Report on Patentability completed on May 21, 2012, in International Patent Application No. PCT/US2010/52376.
International Search Report completed on Jul. 8, 1996, in International Patent Application No. PCT/US96/09005.
International Search Report completed on Nov. 10, 2003, in International Patent Application No. PCT/US02/36735.
International Search Report completed on Nov. 22, 2010, in International Patent Application No. PCT/US2010/052376.
International Search Report completed on Feb. 8, 2011, in International Patent Application No. PCT/US10/52084.
International Search Report completed on Apr. 26, 2011, in International Patent Application No. PCT/US2010/044045.
International Search Report completed on Dec. 21, 2011, in International Patent Application No. PCT/US11/49168.
International Search Report completed on Feb. 12, 2012, in International Patent Application No. PCT/US11/59372.
International Search Report completed on Jun. 18, 2012, in International Patent Application No. PCT/US12/30930.
International Search Report completed on Sep. 24, 2012, in International Patent Application No. PCT/US12/50380.
International Search Report completed on Nov. 9, 2012, in International Patent Application No. PCT/US12/45426.
Jayasinghe et al., "Controlled deposition of nanoparticle clusters by electrohydrodynamic atomization," *Nanotechnology*, 15:1519-1523 (2004).
Jiang et al., "Microfluidic synthesis of monodisperse PDMS microbeads as discrete oxygen sensors," *Soft Matter*, 8:923-926 (2011).
Jo et al., "Surface modification using silanated poly(ethylene glycol)s," *Biomaterials*, 21:605-616 (2000).
Johnson et al., "Regulation of blood flow in single capillaries," *American Journal of Physiology*, 212:1405-1415 (1967).
Kaihara et al., "Silicon Micromachining to Tissue Engineer Branched Vascular Channels for Liver Fabrication," *Tissue Engineering*, 6(2):105-117 (2000).
Kiani et al., "Fluctuations in microvascular blood flow parameters caused by hemodynamic mechanisms," *American Journal of Physiology*, 266(5):H1822-H1828 (1994).
Kikuchi et al., "Modified Cell-Flow Microchannels in a Single-Crystal Silicon Substrate and Flow Behavior of Blood Cells," *Microvascular Research*, 47:126-139 (1994).
Koch et al., "Peripheral blood leukocyte NO production and oxidative stress in multiple sclerosis," *Multiple Sclerosis*, 14:159-165 (2008).
Koch et al., "Duration of Red-Cell Storage and Complications After Cardiac Surgery," *The New England Journal of Medicine*, 358:1229-1239 (2008).
Krogh, "Studies on the physiology of capillaries. II. The reactions to local stimuli of the blood-vessels in the skin and web of the frog," *The Journal of Physiology*, 55:412-422 (1921).
Kuraoka, et al., "Ship-in-a-bottle synthesis of a cobalt phthalocyanine/porous glass composite membrane for oxygen separation," *Journal of Membrane Science*, 286(1-2):12-14 (2006).
Lugowski et al., "Anti-endotoxin antibodies directed against *Escherichia coli* R-1 oligosaccharide core-tetanus toxoid conjugate bind to smooth, live bacteria and smooth lipopolysaccharides and attenuate their tumor necrosis factor stimulating activity," *FEMS Immunology and Medical Microbiology*, 16:31-38 (1996).
Mazor et al., "Prolonged Storage of Red Cells: The Effect of pH, Adenine Phosphate," *Vox Sanguinis*, 66:264-269 (1994).
McDonald et al., "Poly(dimethylsiloxane) as a Material for Fabricating Microfluidic Devices," *Accounts of Chemical Research*, 35(7):491-499 (2002).
Meryman et al., "Prolonged storage of red cells at 4° C.," *Transfusion*, 26(6):500-505 (1986).
Meryman et al., "Extending the storage of red cells at 4° C.," *Transfus. Sci.*, 15(2):105-115 (1994).
Moll et al., "Dean vortices applied to membrane process. Part II: Numerical approach," *Journal of Membrane Science*, 288:321-335 (2007).
Moroff et al., "Proposed standardization of methods for determining the 24-hour survival of stored red cells," *Transfusion*, 24:109-114 (1984).
Murphy et al., "Increased Mortality, Postoperative Morbidity, and Cost After Red Blood Cell Transfusion in Patients Having Cardiac Surgery," *Circulation*, 116:2544-2552 (2007).
Ng et al., "Components for integrated poly(dimethylsiloxane) microfluidic systems," *Electrophoresis*, 23:3461-3473 (2002).
Ohkuma et al., "The preservative-exchange method using a sextuple-bag system for a 10-week storage period of red blood cells," *Transfusion Medicine*, 1:257-262 (1991).
Poxton, "Antibodies to lipopolysaccharide," *Journal of Immunological Methods*, 186:1-15 (1995).
Pries et al., "Biophysical aspects of blood flow in the microvasculature," *Cardiovascular Research*, 32:654-667 (1996).
Sambuceti et al., "Why should we study the coronary microcirculation?," *Am J Physiol Heart Circ Physiol*, 279:H2581-H2584 (2000).
Shimizu et al., "Multicenter Clinical Evaluation of Red Cell Concentrates Stored up to 6 Weeks in MAP, a new additive solution," *Japanese Journal of Clinical Hematology*, 33(2):148-156 (1992).
Skalak et al., "Deformation of Red Blood Cell in Capillaries," *Science*, 164(3880):717-719 (1969).
Sohmer et al., "Phosphoenolypyruvate (PEP) Effects on Fresh and Stored Red Blood Cells," *Proceedings of the Society for Experimental Biology and Medicine*, 171:24-33 (1982).
Sutton et al., "A Novel Instrument for Studying the Flow Behaviour of Erythrocytes through Microchannels Simulating Human Blood Capillaries," *Microvascular Research*, 53:272-281 (1997).
Szymanski et al., "Effect of rejuvenation and frozen storage on 42-day-old AS-1 RBCs," *Transfusion*, 41:550-555 (2001).
The International Committee for Standardization in Hematology, "Recommended Methods for Radioisotope Red Cell Survival Studies," *Blood*, 38(3):378-386 (1971).
Tinmouth et al., "The Clinical Consequences of the Red Cell Storage Lesion," *Transfusion Medicine Reviews*, 15(2):91-107 (2001).
Tracey et al., "A Silicon Micromachined Device for Use in Blood Cell Deformability Studies," *IEEE Transactions on Biomedical Engineering*, 42(8):751-761 (1995).
Tsukada et al., "Direct Measurement of Erythrocyte Deformability in Diabetes Mellitus with a Transparent Microchannel Capillary Model and High-Speed Video Camera System," *Microvascular Research*, 61:231-239 (2001).
Valeri et al., "The survival, function, and hemolysis of human RBCs stored at 4° C. in additive solution (AS-1, AS-3, or AS-5) for 42 days and then biochemically modified, frozen, thawed, washed, and stored at 4° C. in sodium chloride and glucose solution for 24 hours," *Transfusion*, 40:1341-1345 (2000).
Weinberg et al., "Transfusions in the Less Severely Injured: Does Age of Transfused Blood Affect Outcomes?," *The Journal of TRAUMA*, 65(4):794-798 (2008).
Wilding et al., "Manipulation and Flow of Biological Fuids in Straight Channels Micromachined in Silicon," *Clinical Chemistry*, 40(1):43-47 (1994).
Wood et al., "The Viability of Human Blood Stored in Phosphate Adenine Media," *Transfusion*, 7(6):401-408 (1967).
Wu et al., "Polymer microchips bonded by $O_2$-plasma activation," *Electrophoresis*, 23:782-790 (2002).
Yoshida et al., "Extended storage of red blood cells under anaerobic conditions," *Vox Sanguinis*, 92:22-31 (2007).
Yoshida et al., "Storage of red blood cells under anaerobic conditions: reply," *Vox Sanguinis*, 93:184 (2007).
Yoshida et al., "The effects of additive solution pH and metabolic rejuvenation on anaerobic storage of red cells," *Transfusion*, 48:2096-2105 (2008).
Yoshida et al., "Anaerobic storage of red blood cells," *Blood Transfus*, 8:220-236 (2010).
Zhang et al., "Modification of Si(100) surface by the grafting of poly(ethylene glycol) for reduction in protein adsorption and platelet adhesion," *J Biomed Mater Res*, 56:324-332 (2001).
Zimrin et al., "Current issues relating to the transfusion of stored red blood cells," *Vox Sanguinis*, 96:93-103 (2009).
"Cell Deformability," RheoSCAN <http://www.rheoscan.com/products/products_01.html> Seoul, South Korea, pp. 1-4, Retrieved: Jun. 24, 2009.

\* cited by examiner

SYSTEM FOR ASSESSING THE EFFICACY OF STORED RED BLOOD CELLS USING MICROVASCULAR NETWORKS

RELATED APPLICATION

This application is a Continuation-in-part application of U.S. application Ser. No. 10/377,178 filed on Mar. 1, 2003, now U.S. Pat. No. 7,517,453, issued on Apr. 14, 2009, the contents of which are incorporated by reference herein.

BACKGROUND OF THE INVENTION

1. Field of the Invention

The present invention relates to a system for the measurement of the efficacy of stored red blood cells using microvascular devices. More particularly, the present invention relates to microvascular devices that simulate the capillary networks and their physiological function and measurement devices that measure criteria of a sample of previously stored blood to determine the sample's efficacy prior to transfusion.

2. Description of Related Art

In the last few years, several clinical studies have seriously questioned the safety and efficacy of transfusing stored red blood cells (RBCs) in a range of clinical situations [Koch et al. 2008; Weinberg et al. 2008; Murphy et al. 2007, 2008; Zimrin and Hess 2009]. During refrigerated storage, RBCs lose ATP, membrane and volume, change shape, demonstrate a significant reduction of deformability, and, as a result, may become unfit for circulation [Hess and Greenwalt 2002; Zimrin and Hess 2009; Tinmouth and Chin-Yee 2001]. If transfused, these cells may diminish local delivery of oxygen by retarding the flow of blood through larger vessels and by plugging or bypassing the capillaries of microvascular networks, and thus ultimately cause ischemia of tissues and critical end organs [Murthy et al. 2007; Tsai et al. 2004]. So far, physicians have been unable to predict how well RBCs from a particular device of stored blood will perfuse the microvasculature of the patient receiving transfusion.

Human red blood cells (RBCs) are highly deformable 8 μm-in-diameter biconcave disks filled with a concentrated solution of hemoglobin and fine-tuned by evolution to perform their main task—the transport of oxygen and carbon dioxide. In order to accomplish that, RBCs need to pass through the intricate networks of microscopic blood vessels pervading every tissue and organ of the human body. When navigating through the microvascular networks (vessels ranging from 100 to 3 μm in diameter) at physiologically high hematocrits, RBCs must undergo a wide range of deformations. Such deformations include folding in small capillaries and shear deformations in large vessels of the microcirculation. The efficiency of oxygen delivery throughout the body is determined by the level of perfusion of the microvascular networks, which in turn depends on the microvascular fitness of RBCs.

A large number of experimental techniques aimed at quantifying the ability of RBC to deform under various conditions has been developed to date, including ektacytometry, micropipette aspiration, filtration through a polycarbonate or nickel mesh filter, single pore filtration, dragging by optical tweezers, and passage through parallel arrays of capillary-like microchannels.

Each of these methods allows for examination of the behavior of RBCs in response to a particular mode of deformation. While providing valuable information on the rheological properties of RBCs at the most basic level, these measurements are unable to predict how well a sample of RBCs will perfuse networks of microvessels at physiologically high hematorcits and the clinical significance of these measurements remains controversial.

Accordingly, there is a need for a system to help physicians assess the potential efficacy and toxicity of a stored RBCs sample blood prior to transfusion by measuring the ability of stored RBCs perfuse artificial, microfabricated microvascular networks that are structured to simulate human vasculature.

SUMMARY OF THE INVENTION

The present disclosure provides for a system that evaluates the ability of RBCs to perfuse microvascular networks directly, in which an artificial microvascular network device is structured to simulate the structure of the human vasculature. The microvascular network is structured such that the microvascular network device includes a plurality of microchannels that are sized and structured as capillaries of the vasculature.

The present disclosure also provides for a system having an analysis device and a microvascular network that measures and quantifies (i) the overall flow rate of the RBCs through the network, (ii) the flow rates in microchannels) of the network, and (iii) the tube hematocrits in microchannels of the network to determine efficacy of the sample prior to transfusion. The analysis device is able to compare measurements of the sample of RBCs to measurements of known healthy red blood cells to determine the efficacy of the stored sample.

The present disclosure further provides for an artificial microvascular network having an array of interconnected microchannels operating simultaneously in multi- and single-file flow regimes with a wide range of flow rates, for any given operational pressure differential across the network.

The present disclosure still further provides for a system that permits RBCs passing through the network at physiologically high hematocrit to undergo all modes of deformation, including but not limited to folding deformations in capillary-sized microchannels and shear deformations in larger channels—under a variety of different flow conditions, in a manner similar to in vivo microcirculation.

The present disclosure provides for a system having an analysis device and a disposable cartridge or cassette having a microvascular network device that receives a sample of stored blood for analysis. The analysis device is able to obtain and compare measurements of the stored blood to values of known (predetermined) fresh, healthy blood to assess the efficacy of the stored blood prior to transfusion.

A system for assessing the microvascular fitness of a sample of stored red blood cells. The system has a network device and at least one network unit. The network unit has a single inlet and a single outlet for the sample and a plurality of microchannels. The plurality of microchannels receives the sample from the single inlet and drains the sample into the single outlet. The network unit includes an aspiration pressure means for providing movement of liquid sample through the at least one network unit. The system further includes an analysis device that receives the network device therein. The analysis device includes a sensor for capturing measurements related to the sample and a processor capable of comparing the captured measurements to corresponding measurements stored in a database of fresh and healthy red blood cells to determine the microvascular fitness of the stored red blood cells.

A method for assessing the microvascular fitness of a sample of stored red blood cells includes the steps of obtaining and storing measurements from a plurality of samples of healthy and fresh red blood cells. The method further includes flowing a sample of stored red blood cells through a network device and sensing measurements relating to the stored red blood cells. The measurements are compared to determine the microvascular fitness of the stored red blood cells.

A microchannel network device including at least one network unit having a single inlet and a single outlet for the sample. The at least one network unit also includes a plurality of microchannels; wherein the plurality of microchannels receive the sample from the single inlet and drains the sample into the single outlet. An aspiration pressure means is provided for movement of liquid sample through the at least one network device. A substrate disposed beneath the at least one network unit is also provided. Each of the plurality of microchannels is either i) a parent microchannel that branches into two daughter microchannels at an angle of from approximately 20° to 80°, or ii) a convergence of two daughter microchannels at an angle of approximately from 20° to 80° to the convergence channel.

Other features and advantages of the invention will be apparent from the following detailed description, and from the claims.

DETAILED DESCRIPTION OF THE INVENTION

Figure 1:
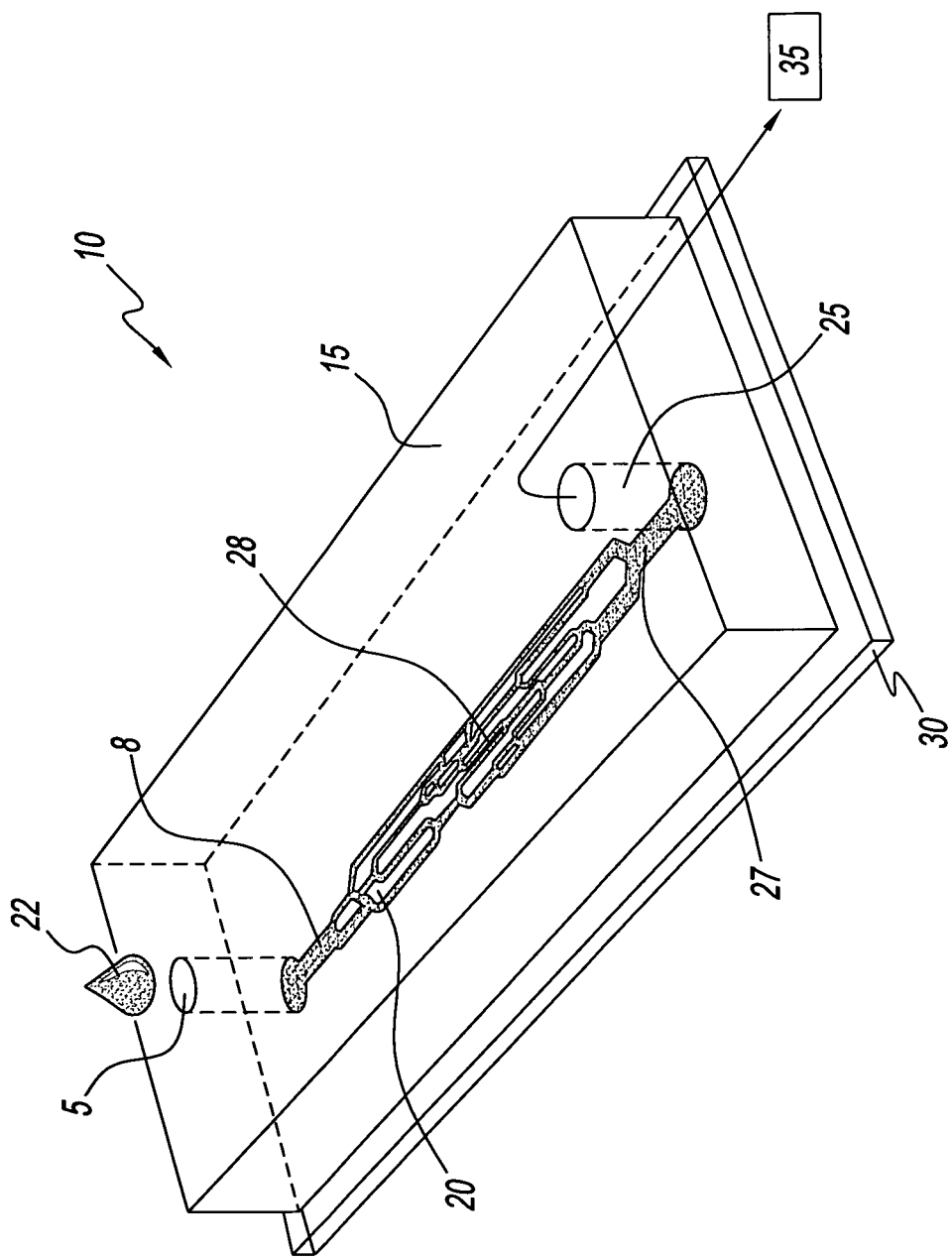
FIG. 1 illustrates a microvascular network device according to the present invention.

Referring to the figures and, in particular, to FIG. 1, the microvascular network device according to the present embodiment is shown, and generally referenced by reference numeral 10. Microchannel network device 10 has a molded component 15 with a network unit 20 molded therein that is sized and structured to mimic the internal human vasculature. Molded component 15 rests directly on slide 30, a substrate, that is a coated slide to ensure closed seal with molded component 15. Microchannel network device 10 has an inlet port 5 and an inlet channel 8 for receipt of a blood sample 22. Microchannel network device 10 has an outlet port 25 and an outlet channel 27 that are operatively associated with a vacuum source 35 to simulate the actual flow of blood in vivo. Network device 10 has a plurality of microchannels 50 that simulate the capillaries of the human vasculature.

Figure 2:
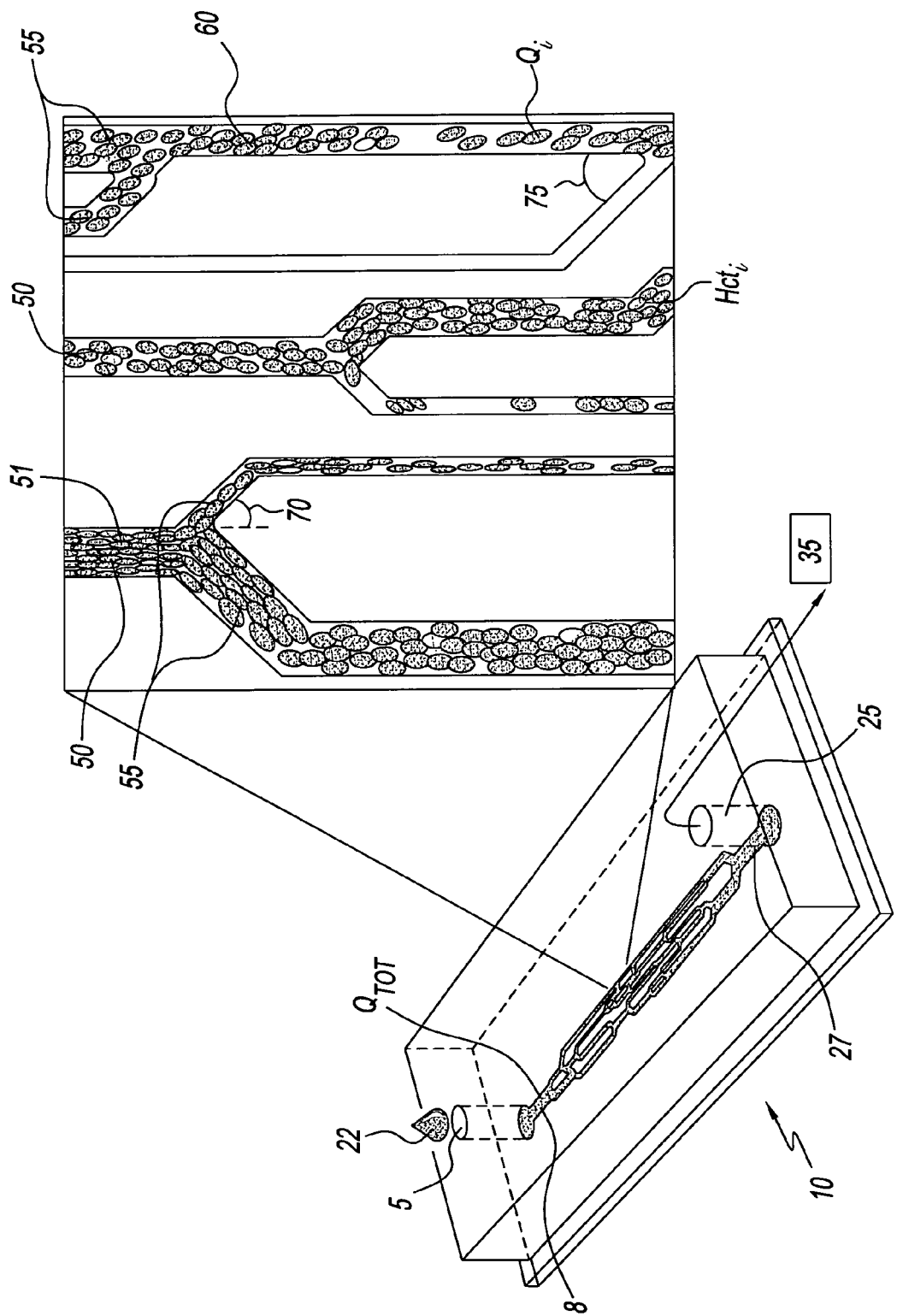
FIG. 2 illustrates an exploded view of a portion of the microvascular network device, of FIG. 1, according to the present invention.

Referring to FIG. 2, showing an enlarged view of network device 10, a plurality of microchannels 50, are shown. Network device 10 has a single inlet port 5 and a single outlet port 25 through which the entire blood sample 22 flows. Each of the plurality of microchannels 50 is either a parent microchannel 51 that feeds and branches into two daughter microchannels 55 or is a convergence channel 60 that results from the convergence of two daughter microchannels 55. Parent channels 51 have a greater cross-sectional area than daughter microchannels 55 and convergence channels 60 have a greater cross-section area than daughter microchannels 55 that feed into the convergence channels 60.

In a preferred embodiment, network device 10 includes thirty-four 6 μm-deep, 70 to 6 μm-wide microchannels, bifurcating at a 45° angle, relative to the inlet of the two bifurcated or daughter channels 55. A different number of microchannels 50 having a variety of dimensions could also be used. In the simplest embodiment, microchannels 50 of the artificial microvascular network device 10 are interconnected in a way mimicking the overall topology of real microvasculature. A bifurcating angle 70 or convergence angle 75 is a 45° angle, although the range for both the bifurcation angle 70 and convergence angle could range from approximately 20° to 80°. Bifurcating angle 70 is measured relative to the angle at which it diverges from the axis of the parent channel 50. A convergence angle 75 is measured relative to the axis at which daughter channels 55 converges with a convergence channel 60. The 45° angle mimics or replicates the internal human vasculature. Were a microchannel network to feed into daughter channels at 90° angles, feed into three daughter channels, or be an entirely straight channel, the actual human vasculature would not be accurately replicated and would not yield reliable results in subsequent analysis.

Figure 3A:
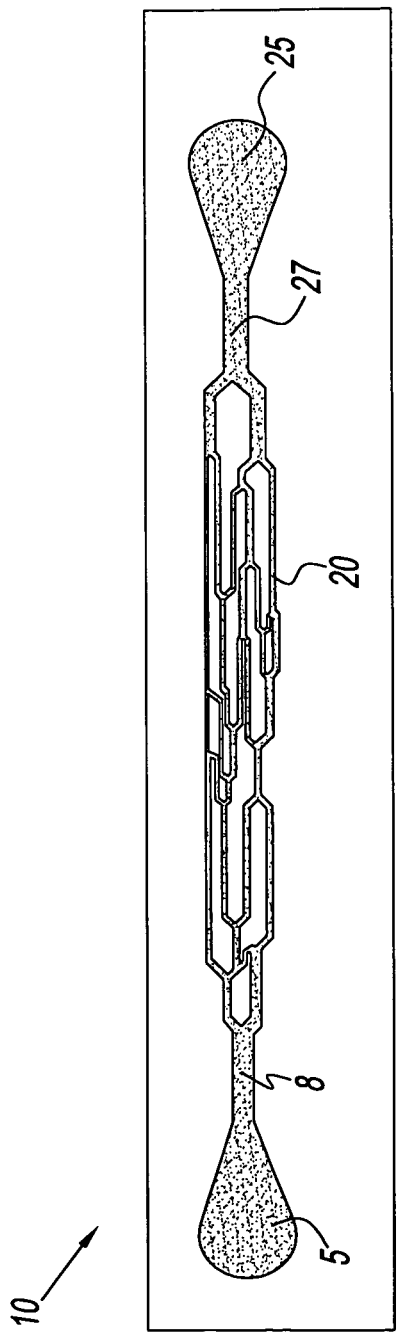
FIGS. 3a and 3b illustrate a top and side view, respectively, of the microvascular network device according to FIG. 1 of the present invention.

Referring to FIG. 3a, inlet port 5 and the outlet port 25, preferably, have a teardrop shape. Inlet channel 8, replicating an arteriole, and outlet channel 27, replicating a venule, are short in length, but are much wider than microchannels 50. The relative size of input channel 8 and output channel 27 are significantly larger, and therefore will have a lower fluidic resistance than microchannels 50.

Figure 3B:
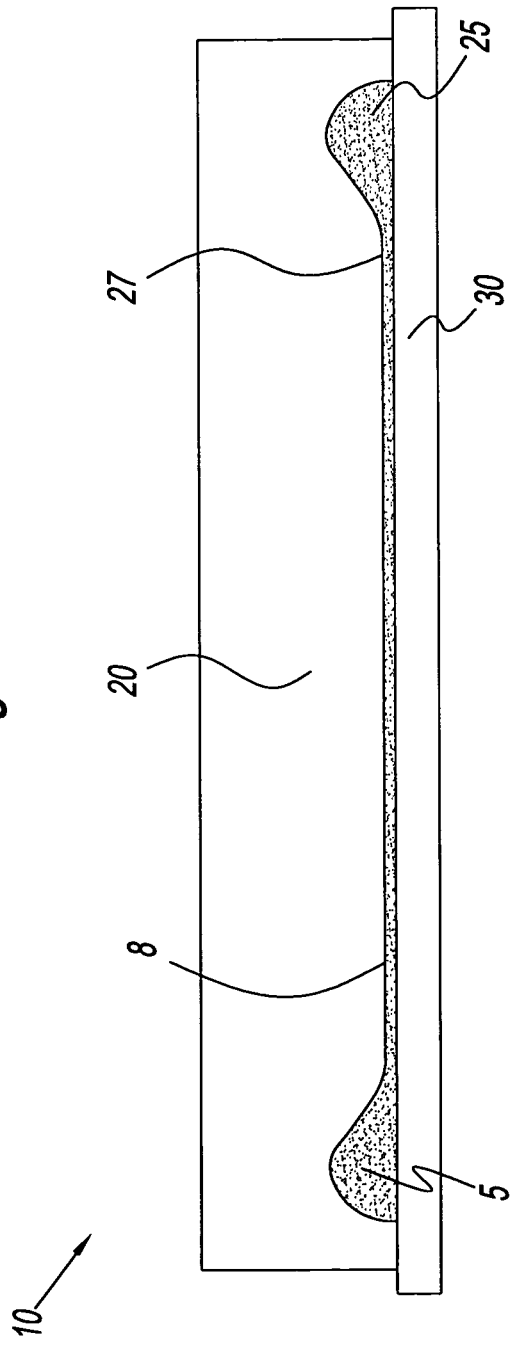

Microchannels 50 can be variable in cross section, such as rectangular or circular or any similar shape. Referring to FIGS. 3a and 3b, the length of the microchannels 50, the region including microchannels 51, 55, and 60, is approximately 1800 μm, although the region could be larger or smaller. The length of inlet channel 8 and outlet channel 27 is approximately 300 μm, although the length could vary. The inlet port 5 and the outlet port 25 are tear-shaped and substantially larger than the other components of network device 10. The dimensions of the inlet port 5 and the outlet port 25 are approximately 5000 μm in length and 500 μm in depth. Preferred samples for use in the network device 10 may be selected from the group consisting of: cells, microorganisms, and any combinations thereof suspended in an appropriate solution. Preferred samples are whole blood, white blood cells with or without plasma (diluted or undiluted), and most preferably red blood cells and platelets with or without plasma (diluted or undiluted).

Figure 4B:
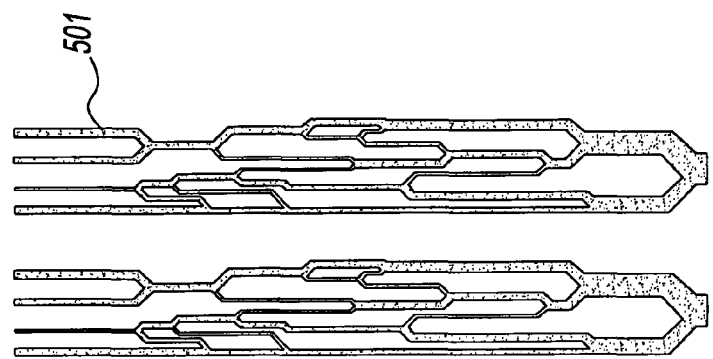
FIGS. 4a and 4b illustrate a larger microvascular network device, according to a further embodiment of the present invention.
Figure 4A:
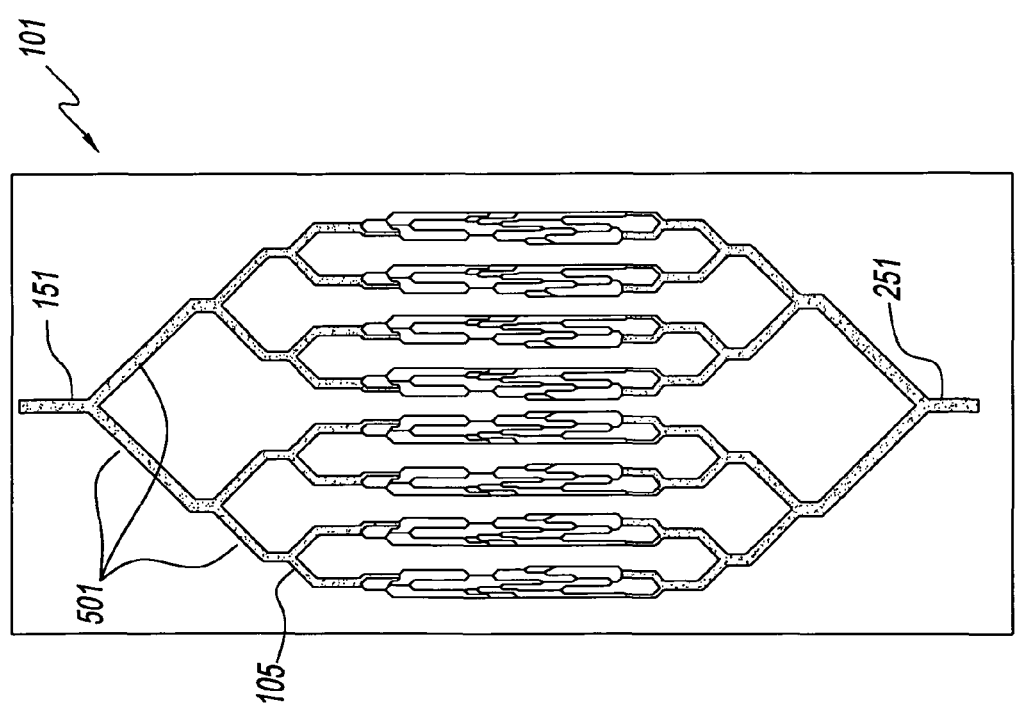

In a further embodiment shown in FIGS. 4a and 4b, network device 101 is larger and a network unit 105 having more microchannels 501 than microchannel device 10. However, network device 101 also has a single inlet channel 151 and a single outlet channel 251. Such network 101 can be used to enhance performance by having greater sensitivity. Network device 101 is structured in the same way as network device 10. Thus, it too replicates the human vasculature by having bifurcating microchannels.

Other embodiments of the network may mimic the actual microvascular networks of specific tissues and end organs (including, by not limited to, heart, retina of the eye, brain, kidney), the microvascular networks of said tissues and organs at various development stages as well as tumors. Morphometric information regarding the geometrical dimensions of the microvessels of the microvascular networks of these organs and the topological information about how these microvessels connect to form these networks would be used in and fabricating an artificial microvascular network with all of the organ-specific characteristics.

There are three primary measurements that are significant to the measurement of perfusion of blood for analysis prior to transfusion. One such measurement is overall flowrate $Q_{tot}$. The overall flow rate through the network provides a general assessment of how well a sample of stored RBCs is able to perfuse the microvascular network device 10, 101. The overall rate of flow of blood sample through the network is determined by measuring the rate of flow of RBCs in the inlet channel 8 to the outlet 27 of network device 10, for example.

The measurement of the overall rate of flow of blood sample through network device 10, 101 provides an integrative measurement of the sample's performance. Any changes in the fluidic resistance of the network to the flow of blood due to a reduction (or an improvement) in the microvascular fitness of the sample 22 will be reflected in this measurement. Referring to FIG. 1, network device 10 having one inlet port 5 and one outlet port 25, the rate of flow in inlet port 5 (arteriole) and the rate of flow in outlet port 25 (venule) are identical. The flow rate of blood sample in network device 10 is determined by measuring the average sample velocity via frame-by-frame image analysis. A sensor is used to capture images (frames) of the channel at precisely known intervals. Regions within the channel walls from two sequential frames are cross-correlated to determine how far RBCs in a microchannel have shifted (on average) in the time interval between the two sequential frames. The distance that RBCs have shifted or traveled then divided by the time interval to calculate the average RBC velocity in the channel.

Figure 5:
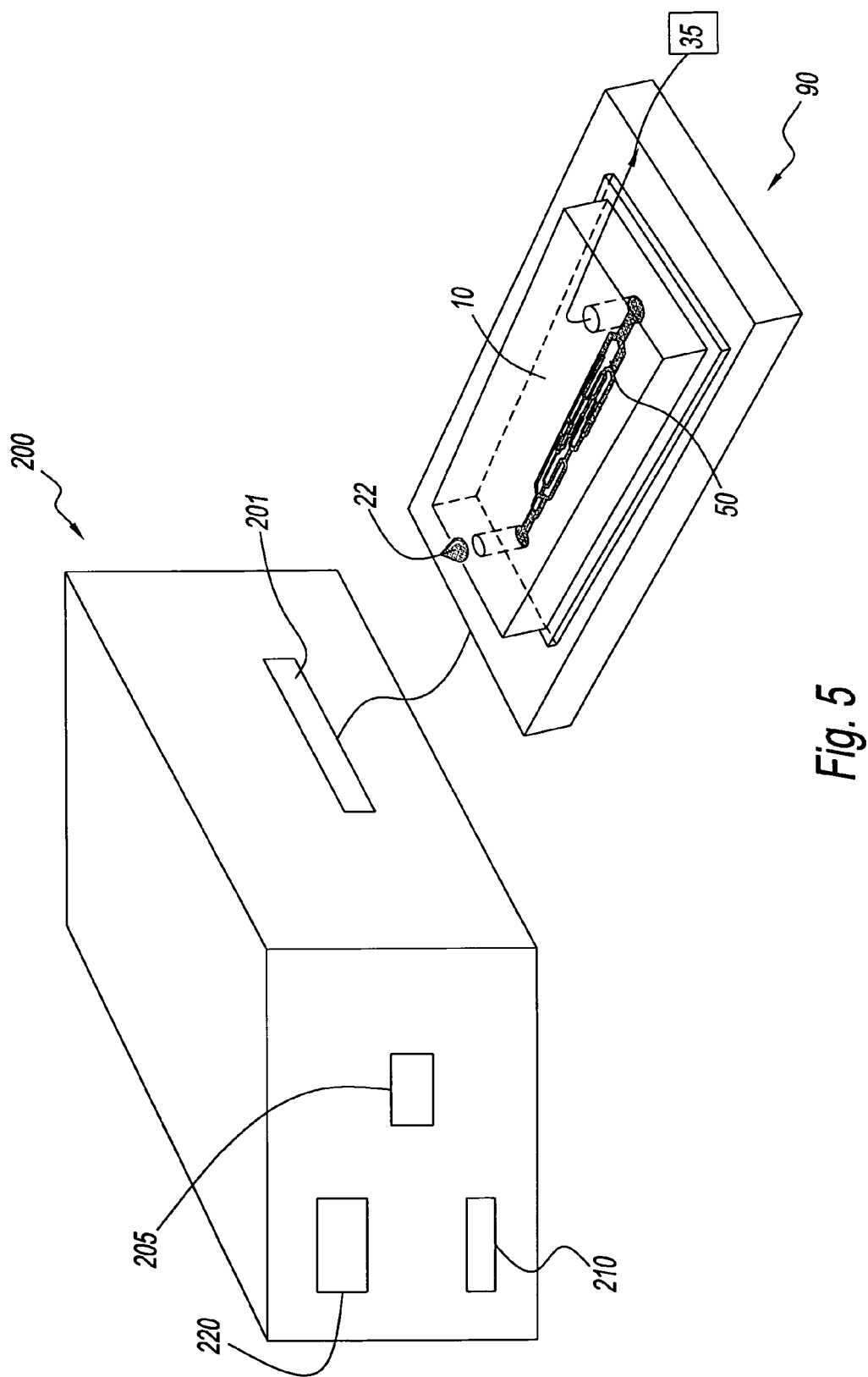
FIG. 5 illustrates a microvascular network device incorporated into an analysis device that measures the overall flow rate through the network, the microchannel flow rates in microchannels and hematocrits in microchannels, for a sample in the microvascular network, according to the present invention.

Referring to FIG. 5, network device 10 (and 101) is preferably a disposable element of a cartridge or cassette 90 that is inserted into an analysis device 200 that is able conduct measurements on the blood sample that flows through plurality of microchannels 50 of microvascular network device 10. Analysis device 200 contains a receptacle 201 that receives network device 10 for analysis. Analysis device 200 preferably contains a sensor 205, that is able to capture frames or data related to sample as it flows through microchannels 50. Analysis device 200 has a memory device 210 into which captured frames or data can be stored for later reproduction as a video and for analysis. Sensor 205 captures images or frames of blood along at least two locations along network device 10. The flow rates can be measured by performing frame-by-frame image analysis of the high-speed movies of the flow of blood in the network by sensor 205 contained within analysis device 200. Analysis device 200 also has a processor 220 to carry out the computations related to the captured frames or data. Sensor is preferably one of a CCD or CMOS digital camera, a pair of photodiodes and an ultrasonic transducer that are configured to sense the sample as it passes through device 10, 101.

Additionally, analysis device is 200 is able to capture and store measurement data in a database of memory device 210 that includes measurements of a plurality of healthy blood samples for purposes of comparison to a stored blood sample to determine the vascular fitness of the stored sample. The plurality of healthy blood samples are hundreds of fresh, healthy blood samples. The stored measurements of healthy samples can optionally be stored according to characteristics of the individual from whom the healthy sample is taken for further comparison to stored samples.

In a specific embodiment, the image acquisition system consisted of an Olympus BX51 microscope with an attached high-speed digital CMOS camera (Silicon Video 2112; Epix, Inc.) and a frame grabber board (PIXCI D2X; Epix, Inc.) mounted in a dedicated PC (Dimension XPS D300, Dell). Frame sequences were captured in computer memory and saved on hard drive (XCAP-Lite; Epix, Inc.) for analysis using custom software written in MATLAB (Mathworks, Inc.) or in C++(Microsoft Visual C++6.0; Microsoft, Corp.). Compatible equipment would also be used with either a photodiode or an ultrasound device as well. The same analysis is performed with means other than the digital camera, for example by analyzing the signal from a photodiode or using ultrasound means for measuring the average velocity of the sample of RBCs in the microchannel.

A further measurement that is critical to the determination of efficacy of stored blood is the measurement of the rate of flow of blood in every microchannel 50 $Q_i$ of the network device 10. The flow rates in individual capillary-sized microchannels 50 provide a measure of how well stored RBCs are able to reach the smallest vessels of the microvasculature to complete the delivery of oxygen. The measurement of the distribution of the rates in microvascular channels 50 of the network 10 provides a much more detailed and a different kind of information regarding the microvascular performance of the blood sample than the overall flow rate $Q_{tot}$. A reduction in the capillary flow rates (with respect to a sample of fresh blood) would indicate a poor quality of stored blood being tested even if the overall flow rate through the network is approximately the same. The flow rate of blood sample 22 in microchannels 50 is measured in the same fashion as the overall flow rate $Q_{tot}$ is measured.

A third measure of the fitness of stored blood is, tube hematocrist $Hct_t$ in the capillary microchannels of the network. Tube hematocrits provide a further independent measure of how well stored RBCs are able to reach the microchannels 50, 501 of microvascular devices 10, 101. When this measurement is combined with the measurements of capillary flow rate $Q_i$, the oxygen carrying capacity and other biochemical characteristics of stored red blood cells of sample 22, an estimate of the actual rate of oxygen delivery to tissues is provided.

The tube hematocrit in a channel in a microchannel 55 of FIG. 1, for example, is determined by measuring via image analysis the transmittance of blue light (415±15 nm) passing therethrough. Because hemoglobin inside of the RBCs of sample 22 adsorbs blue light very well, RBCs appear dark when illuminated with blue light and their volume concentration in the channel (i.e., tube hematocrit) correlates well with the "darkness" of the channel. Because of hemoglobin, RBCs appear dark in blue light—the use of a narrow band-pass blue filter (415±15 nm) to match hemoglobin's Soret absorption band facilitates the measurement of tube hematocrit in microchannels 55, for example, of the device 10.

Thus, $Q_{tot}$, the total rate of flow through network device 10, $Q_i$, flow in particular microchannels, and $Hct_t$, the tube hematocrit in each individual microchannel of device 10 provide valuable information of the fitness of the RBCs in a sample 22. The pressure differential across network 10, is kept constant during the measurement. For different measurements, the pressure across the network 10 could be varied between different measurements and during an individual measurement.

These three measurements made by using analysis device and network devices 10, 101 of the present disclosure are part of an array of parameters that allow the estimation of the efficacy of a stored blood sample.

In order to determine the microvascular fitness of a sample of stored blood, the microvascular fitness of fresh healthy blood is used as the standard for comparison to previously stored blood samples prior to transfusion. Thus, actual ranges of these three measurements will be determined experimentally by passing fresh, normal, healthy blood through network 10 to obtain a set of pre-determined or standard values for healthy blood. The three measurements of healthy, fresh, normal blood of hundreds of individuals may be stored and used as the standard for subsequent measurements. Measurements of samples of stored RBCs will always be compared to this normal standard.

Thus, to measure the ability of stored RBCs to perfuse microvascular networks (termed "microvascular fitness" in this text), a sample of stored RBCs at physiologically high hematocrit is passed through microchannel network device 10 under a constant pressure differential from inlet port 5 to outlet port 25. The perfusion of sample 22 is evaluated by measuring: (i) the overall rate of flow through the network ($Q_{tot}$) for the constant or varying pressure difference between the inlet and the outlet, (ii), the flow rates ($Q_i$) in the microchannels, and (3) the tube hematocrit ($Hct_i$) of the microchannels. The measurement of network perfusion for sample 22 is then compared to the previously established standard values for fresh healthy RBCs to determine the level of microvascular fitness of the sample of stored RBCs relative to the normal fresh RBCs. Thus, the comparison provides a qualitative indication of the stored sample of RBCs relative to the fresh RBCs to access microvascular.

The sample RBCs 22 were preferably washed three times in phosphate buffered saline (PBS) and passed through a leukoreduction filter to reduce the concentration of white blood cells (WBC) and platelets. Washed cells were diluted into GASP buffer (containing 9 mM $Na_2HPO_4$, 1.3 mM $NaH_2PO_4$, 140 mM NaCl, 5.5 mM glucose, and 1% bovine serum albumin, pH 7.4, osmolarity 290 mmol/kg), or in other buffers. The hematocrit of sample 22 in GASP is adjusted to a specific value (often 40%), sample size was 20 μl and experiments were performed at room temperature. This is not to exclude the possibility of different sample sizes, different hematocrits and running measurements at different temperatures as well.

In addition to optional washing steps, a chemical or drug may be introduced to observe its effects in altering deformability of RBCs in sample 22. A chemical reaction induced by a drug may result in subtle changes in fluidity or mechanical properties of sample 22, namely RBC membrane or RBC cytosol. Devices 10, 101 can evaluate the effects of these treatments on deformability and perfusability. It should be also noted that a blood from some individual could behave differently from the population average under external chemical treatment. For example, a relatively common glucose 6 phosphate dehydrogenase deficiency phenotype would be severely affected by an oxidative stress which may be introduced by the treatment with antimalarial drugs such as primaquine, and may significantly change the ability of the treated red blood cells to perfuse the microvascular network of device.

Range for pressure differential along the network, the difference in pressure from the inlet to the outlet ranges from 0 mmHg to 250 mmHg (340 cmH2O). The highest limit corresponds to the systolic blood pressure in severe hypertension (stage 4). In the venous part of systemic circulation blood pressure is normally about 10 mmHg (14 cmH2O). The pressure difference between the arteriole (inlet) and the venule (outlet) of a microvascular bed is normally on the order of 30 mmHg (40 cmH2O)

The overall flow $Q_{tot}$ and the individual flow rate $Q_i$ in each microchannel network 50 are each measured in the devices in the dimensional units of microliters per minute (uL/min). A normal range for each measurement is determine by the values for fresh normal healthy RBCs an can be from 0 uL/min to 100 uL/min. The normal range may depend on the specific network used in the measurement.

The following chart provides the normal ranges of sample hematocrit (systemic hematocrit) for subjects of various ages. The tube hematocrit in microchannels 50, 51, 55 and 60 of the microvascular network may be higher and lower than the value of the sample hematocrit.

| NORMAL TUBE RANGES FOR SYSTEMIC HEMATOCRIT (Hct) | |
|---|---|
| Newborns | 55%-68% |
| One (1) week of age | 47%-65% |
| One (1) month of age | 37%-49% |
| Three (3) months of age | 30%-36% |
| One (1) year of age | 29%-41% |
| Ten (10) years of age | 36%-40% |
| Adult males | 42%-54% |
| Adult women | 38%-46% |

The microchannel network devices 10, 101 include several interconnected microchannels 50, 501 operating in multi- or single-file flow regimes with a wide range of flow rates. Sample 22 having RBCs flowing through the microchannel network devices 10, 101 at natural hematocrit would undergo all modes of deformation—folding and in shear in microchannels 50, 501 under a variety of different flow conditions, similar to the real microcirculation. The information provided from analysis device 200 permits a straightforward interpretation by the physicians making the decision regarding transfusion and, therefore, could produce an immediate clinical value.

Microvascular network devices 10, 101 of the present application has applicability to the study of pathological conditions. Thus, sample RBCs in which the red cell is more rigid because of diabetes mellitus, red cells that are infected with parasitic forms as occur in malaria, red cells that demonstrate genetic abnormalities, such as those found in thalassemia and sickle cell decease, i.e., may also be used. Further, cells which display the changes of metabolic or parasitic diseases and other pathological processes that involve the formed elements and any combinations thereof, may also be studied using the microvascular network devices 10, 101 of the present disclosure.

To manufacture network devices 10, 101, a master silicon wafer is used. The configuration of microvascular network device 10 is transferred onto a master silicon wafer (not shown) using a direct laser writer (Heidelberg DWL 66, Heidelberg Instruments Mikrotechnik GmbH) and reactive ion etching (Bosch process, Unaxis SLR 770 ICP Deep Silicon Etcher, Unaxis USA Inc). The master wafer may also be fabricated using photolithography of SU-8 photoresist or other photosensitive material. Features on the silicon wafer are inversed relative to the design of network 20 of network device 10. Recessed areas of the master wafer correspond to the microchannels 50 of network device 10. The master wafer fabricated in this manner can be replica-molded many times to produce microfluidic devices in materials such as for example, poly(dimethyl siloxane) (PDMS, produced by either G.E. Silicones as RTV 615 A/B, or by Dow Corning as Sylgard 184).

The pattern on the master wafer is imprinted in PDMS by pouring PDMS pre-polymer over the master wafer and allowing it to cure in an oven at the temperature of 65° C. overnight.

To remove the PDMS replica from the master wafer, the replica is cut with a scalpel and then peeled off from the master wafer. The PDMS replica is then placed onto a clean surface of slide 30 with the molded features facing up to become molded component 15. The inlet port 5 an outlet port 25 are created by locating the inlet and outlet channels of the network 20 molded in the PDMS, and punching through upper component at these locations with a sharp, cylindrical punch (such as a disposable biopsy punch). Outlet port 25 is connected to a waste-collecting reservoir with a PE tubing— such that the blood sample flows from the inlet reservoir, through the network, and exists the device through the outlet at the top of the device. In this embodiment, slide 30 does not to be pre-drilled with a through hole for the outlet.

Molded component 15 contains the actual ceiling and sidewalls of the microchannels of the network 20. Molded component 15 is sealed to slide 30 to form a complete microfluidic device. To assemble the network device 10, molded component 15 and PDMS-coated slide 30 are exposed to air plasma for 100 seconds (Plasma Cleaner/Sterilizer, Harrick Scientific Corporation), affixed together, and placed in an oven at 65° C. for 15 min to complete the covalent bonding of the two contact surfaces. Immediately following assembly, network device 10 is filled with 1% (wt/vol) aqueous solution of mPEG-silane (Laysan Bio, Inc.), and then washed and incubated with GASP buffer (1% bovine serum albumin (BSA), 9 mM $Na_2HPO_4$, 1.3 mM $NaH_2PO_4$, 140 mM NaCl, 5.5 mM glucose, pH 7.4, 290 mmol/kg) to passivate the walls of the channels and prevent adhesion of blood cells to the walls.

Figure 6:
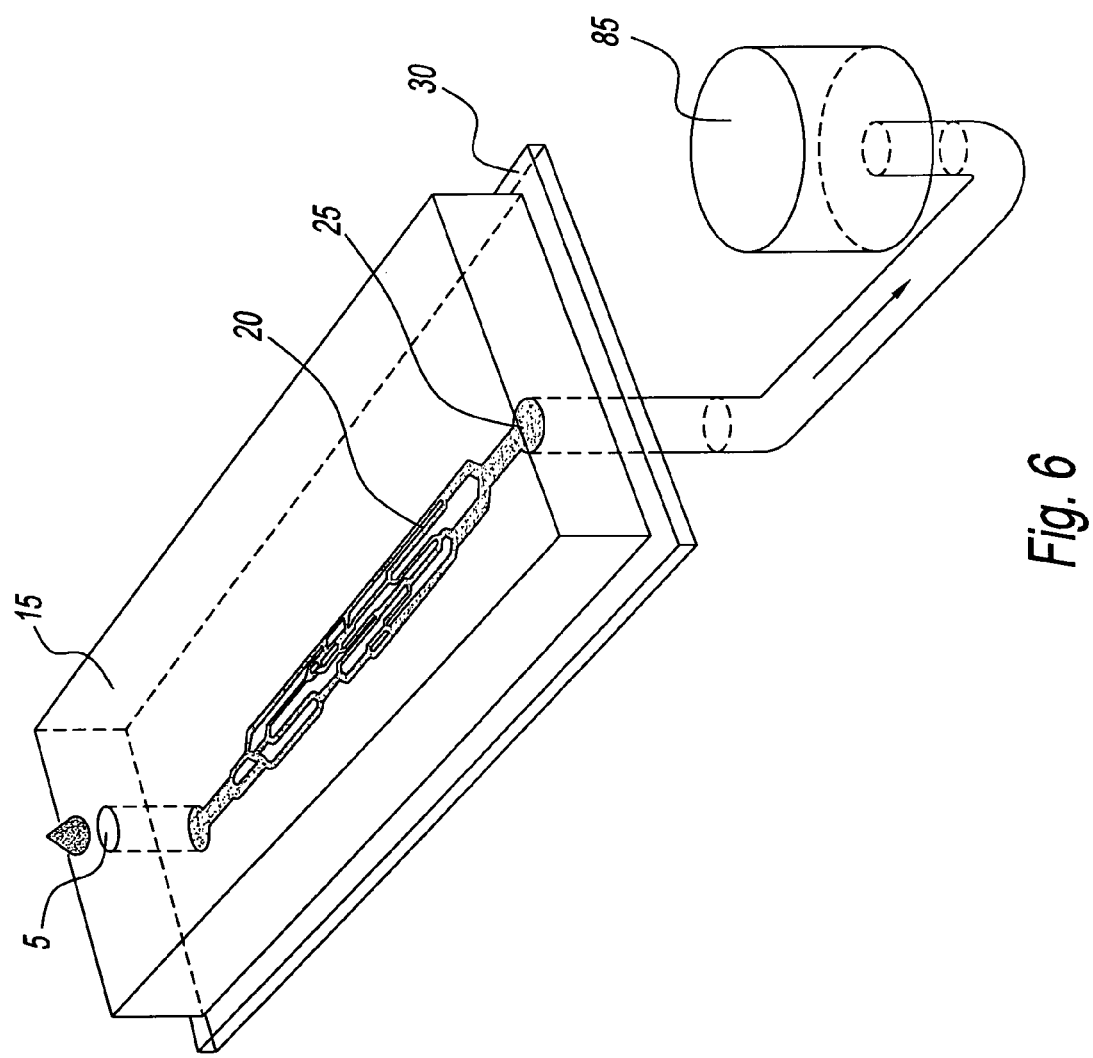
FIG. 6 illustrates a microvascular network device, including a waste reservoir according to the present invention.

In an alternative embodiment shown in FIG. 6, outlet port 25 is not punched through molded component 15 as shown in FIG. 1. In contrast, molded component 15 is sealed against slide 30 that has a 2-mm pre-drilled hole 80. In this particular embodiment, the distal end of output channel 28 is placed directly above hole 80, serving as the output port and connecting the microchannel network device 10 to a large waste-collecting reservoir 85. The pressure differential across network device 10 in this embodiment is regulated by adjusting the relative levels of liquid in the waste-collecting reservoir 85 and the input reservoir of device 10. This embodiment permits modification to the pressure differential to be realized over network 10 so that sample behavior in deformation and shear can be measured over several pressure differentials.

The substrate of the microvascular network device is comprised of glasses, plastics, polymers, metals, ceramics, organic materials, inorganic materials, and any combinations thereof. A preferred substrate is transparent and readily uses the microchannel formation. The device preferably has a plurality of microchannels each having a diameter or width (and as well a depth) from about 1 micrometer to about 100 micrometers.

However, neither the invention substrate nor the microchannel material is limited to any specific material, but may use any material that satisfies the structural and functional requirements of the invention. For example, any material that can be cast into microchannel networks may be employed. A wide spectrum of materials can be used for channel castings. The microchannel material is preferably not hostile to blood cells, especially red blood cells, and may optionally bind lubricant material that may be useful to facilitate cell movement. For example, PEG, mPEG-silane, and the like may be used to coat microchannels.

The prototype model system has applications in a variety of microvascular network studies. This would include studies on the robustness of network function in the presence of elevated white cell counts or cellular aggregates. The former is a physiological response to bacterial infection or a pathological manifestation of neoplastic transformation of leukocyte precursors. The latter occurs in association with diabetes or other hypercoagulable states and may cause or accompany vascular occlusions that can damage heart or brain tissues. Using available pattern generation capabilities, a range of microvascular network designs and complexities can be studied. Computer simulations have shown that plasma skimming and the Fahraeus-Lindqvist effect might entirely account for nonlinear temporal oscillations in microvascular blood flow in the absence of biological regulation. This question can be directly studied and simulated with the device of the invention.

Some microvascular regulatory agents, such as NO, have documented effects on red cell deformability which could effect microvascular flow dynamics and even serve as an independent mechanism for its regulation. The nonlinear dynamics of local blood flow and its dynamic regulation at the local level are also directly studied and simulated with the device of the invention. By modifying the device to include a drug injection port, more precise measurements of dose response relationships and latencies for the effects of such regulatory agents on RBC properties and behaviors in microvascular networks can be obtained. The present invention is also a useful validation tool for earlier computer simulations and theoretical models.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patents, and other references mentioned herein are incorporated by reference in their entirety. In case of conflict, the present specification, including definitions, will control. In addition, the materials methods, and examples are illustrative only and not intended to be limiting of the invention Although the present invention describes in detail certain embodiments, it is understood that variations and modifications exist known to those skilled in the art that are within the invention. Accordingly, the present invention is intended to encompass all such alternatives, modifications and variations that are within the scope of the invention as set forth in the following claims.

We claim:

1. A system comprising:
   a network device comprising:
   an inlet;
   an outlet;
   at least one network unit in fluid communication with said inlet and said outlet comprising a plurality of microchannels,
   wherein said plurality of microchannels comprises
   i) at least one parent microchannel branching into two daughter microchannels of unequal diameter or width, at least one of said two daughter microchannels branching at an angle from approximately 20° to approximately 80°, measured relative to the axis of said at least one parent channel, and
   ii) at least one converged microchannel converging from two microchannels at an angle from approximately 20° to approximately 80°, measured relative to the axis of said at least one converged microchannel; and an analysis device comprising:
one or more sensors configured to capture measurements related to a sample of blood cells flowing from said inlet to said outlet when said system is in use; and
a processor comprising a memory device for determining the microvascular fitness of said sample of blood cells based on said measurements.

2. The system of claim 1, wherein each of said two daughter channels bifuricates from said at least one parent microchannel at an angle from approximately 20° to approximately 80°.

3. The system of claim 1, wherein each of said two microchannels converges at an angle from approximately 20° to approximately 80° to said converged channel.

4. The system of claim 1, wherein said measurements are selected from the group consisting of overall flow rate, microchannel flow rate, tube hematocrit, and any combinations thereof.

5. The system of claim 4, wherein said overall flow rate is determined by measuring flow rate of said sample of blood cells at said inlet and at said outlet of said at least one network device.

6. The system of claim 4, wherein said microchannel flow rate is measured in one or more of said plurality of microchannels.

7. The system of claim 4, wherein said hematocrit is measured in one or more of said plurality of microchannels.

8. The system of claim 1, wherein said network device is formed of at least one material selected from the group consisting of: glass, plastic, polymer, metal, ceramic, organic material, inorganic material, and any combinations thereof.

9. The system of claim 1, wherein each of said plurality of microchannels has a diameter or width in the range between about 6 μm to about 63 μm.

10. The system of claim 1, wherein said sample of blood cells is selected from the group consisting of fresh whole blood, fresh leukoreduced blood, fresh leukoreduced and platelet reduced blood, fresh platelet reduced blood, fresh white blood cells, fresh packed white blood cells, fresh red blood cells, fresh packed red blood cells, stored whole blood, stored leukoreduced blood, stored leukoreduced and platelet reduced blood, stored platelet reduced blood, stored white blood cells, stored packed white blood cells, stored red blood cells, and stored packed red blood cells.

11. The system of claim 10, wherein said sample of blood cells is selected from the group consisting of fresh whole blood, fresh red blood cells, fresh packed red blood cells, stored whole blood, stored red blood cells, and stored packed red blood cells.

12. The system of claim 1, wherein said memory device is further configured to store measurement data of overall flow rate, microchannel flow rate, and tube hematocrit for comparison to said sample of blood cells.

13. The system of claim 1, wherein said one or more sensors is selected from the group consisting of a camera, a pair of photodiodes, an ultrasonic transducer, and combinations thereof, for obtaining images of said sample of blood cells flowing from said inlet to said outlet in said plurality of microchannels when said system is in use.

14. The system of claim 1, wherein said plurality of microchannels comprises dimensionally homogenous cross-sections along any one of said microchannels.

15. The system of claim 1, wherein said plurality of microchannels comprises dimensionally heterogeneous cross-sections along any one of said microchannels.

16. The system of claim 1, wherein said network device further comprises a substrate.

17. A method for assessing the microvascular fitness of a sample of blood cells comprising:
obtaining and storing measurements from a plurality of samples of healthy blood cells;
flowing a sample of blood cells through a network device and sensing measurements related to said sample of blood cells with an analysis device; and
comparing measurements obtained from said plurality of samples of healthy blood cells to measurements derived from said sample of blood cells with said analysis device to determine the microvascular fitness of said sample of blood cells,
wherein said network device comprises:
an inlet;
an outlet;
at least one network unit in fluid communication with said inlet and said outlet comprising a plurality of microchannels,
wherein said plurality of microchannels comprises
i) at least one parent microchannel branching into two daughter microchannels of unequal diameter or width, at least one of said two daughter microchannels branching at an angle from approximately 20° to approximately 80°, measured relative to the axis of said at least one parent channel, and
ii) at least one converged microchannel converging from two microchannels at an angle from approximately 20° to approximately 80°, measured relative to the axis of said at least one converged microchannel, and
wherein said analysis device comprises:
one or more sensors configured to capture measurements related to said sample of blood cells flowing from said inlet to said outlet; and
a processor comprising a memory device for determining the microvascular fitness of said sample of blood cells based on said measurements.

18. The method of claim 17, wherein said obtaining is flowing said plurality of samples of healthy blood cells through said network device and sensing said measurements from a plurality of samples of healthy blood cells with said analysis device.

19. The method of claim 18,
wherein said one or more sensors comprises a sensor that captures images of said sample of blood cells flowing in said network devices;
said analysis device stores said images; and
said processor accesses said images from said storage device and calculates measurement derived from said images of said healthy blood cells and said stored blood cells.

20. The method of claim 19, wherein each of said two daughter channels bifuricates from said at least one parent microchannel at an angle from approximately 20° to approximately 80°.

21. The method of claim 19, wherein each of said two microchannels converges at an angle from approximately 20° to approximately 80° to a convergent channel.

22. The method of claim 17, wherein said measurements from said plurality of samples of healthy blood cells and said sample comprise overall flow rate, microchannel flow rate and tube hematocrit.

23. The method of claim 22, wherein said overall flow rate is determined by measuring flow rate of said sample at said inlet and at said outlet of said network device.

24. The method of claim 22, wherein said microchannel flow rate is measured in one or more of said plurality of microchannels.

25. The method of claim 22, wherein said hematocrit is measured in one or more of said plurality of microchannels.

26. The method of claim 19, wherein said one or more sensors is selected from the group consisting of a camera, a pair of photodiodes, an ultrasonic transducer, and combinations thereof, for obtaining images of said flowing sample in said plurality of microchannels.

27. A device comprising:
   at least one network unit comprising
      a single inlet;
      a single outlet; and
      a plurality of microchannels receiving a sample from said single inlet and drains said sample into said single outlet;
   and
   a substrate disposed beneath said at least one network unit, wherein said plurality of microchannels comprises i) at least one parent microchannel that branching into two daughter microchannels of unequal diameter or width, at least one of said two daughter microchannels branching at an angle from approximately 20° to approximately 80°, measured relative to the axis of said at least one parent microchannel, and ii) at least one converged microchannel converging from of two daughter microchannels at an angle from approximately 20° to approximately 80°, measured relative to the axis of said at least one converged microchannel.

28. The device of claim 27, wherein said plurality of microchannels has a diameter or width in the range between about 6 μm to about 63 μm.

29. The device of claim 27, wherein said sample is selected from the group consisting of fresh blood and stored red blood cells.

30. The device of claim 27, wherein said sample is whole blood.

31. The device of claim 27, wherein said sample comprises red blood cells.

32. The method of claim 27, wherein said plurality of microchannels are selected from the group consisting of: one or more microchannels comprising dimensionally homogeneous cross-sections along said one or more microchannels, one or more microchannels comprising dimensionally heterogeneous cross-sections along said one or more microchannels, and combinations thereof.

33. The device of claim 27, wherein said at least one network unit is a molded network unit.

34. The device of claim 27 being molded from a material selected from the group consisting of: glass, plastic, polymer, metal, ceramic, organic material, inorganic material, and any combinations thereof.

35. The system of claim 1, further comprising a narrow band pass filter for measuring the hematocrit of said sample of red blood cells.

36. The system of claim 1, wherein said one or more sensors is selected from the group consisting of a photodiode, an ultrasonic transducer, and combinations thereof, for measuring the average velocity of said sample of red blood cells in said plurality of microchannels.

37. The system of claim 1, wherein said angle is 45°.

38. The device of claim 27, wherein said angle is 45°.

* * * * *